(12) United States Patent  (10) Patent No.: US 7,970,174 B2
Goldbach  (45) Date of Patent: Jun. 28, 2011

(54) MEDICAL MARKER TRACKING WITH MARKER PROPERTY DETERMINATION

(75) Inventor: Günter Goldbach, Wörth/Wifling (DE)

(73) Assignee: Brainlab AG, Feldkirchen (DE)

( * ) Notice: Subject to any disclaimer, the term of this patent is extended or adjusted under 35 U.S.C. 154(b) by 1037 days.

(21) Appl. No.: 11/767,855

(22) Filed: Jun. 25, 2007

(65) Prior Publication Data

US 2008/0317281 A1 Dec. 25, 2008

Related U.S. Application Data

(60) Provisional application No. 60/820,119, filed on Jul. 24, 2006.

(30) Foreign Application Priority Data

Jun. 27, 2006 (EP) .................................... 06013190

(51) Int. Cl.
 *G06K 9/00* (2006.01)
 *A61B 5/05* (2006.01)
(52) U.S. Cl. ........................................ 382/103; 600/426
(58) Field of Classification Search .................. 382/128, 382/129, 130, 131, 132, 133, 134; 378/4, 378/21–27, 101, 98.4, 98.6, 901; 600/407, 410, 420, 423, 424, 425, 426, 427, 429; 128/920, 922

See application file for complete search history.

(56) References Cited

U.S. PATENT DOCUMENTS

| | | | | |
|---|---|---|---|---|
| 5,951,475 | A * | 9/1999 | Gueziec et al. | 600/425 |
| 6,621,889 | B1 * | 9/2003 | Mostafavi | 378/65 |
| 6,738,656 | B1 * | 5/2004 | Ferre et al. | 600/426 |
| 7,587,234 | B2 * | 9/2009 | Owens et al. | 600/420 |
| 2003/0174401 | A1 | 9/2003 | Brunner et al. | |
| 2003/0225329 | A1 | 12/2003 | Rossner et al. | |
| 2005/0049485 | A1 | 3/2005 | Harmon et al. | |

FOREIGN PATENT DOCUMENTS

DE  196 39 651  4/1998

* cited by examiner

*Primary Examiner* — Abolfazl Tabatabai
(74) *Attorney, Agent, or Firm* — Renner, Otto, Boisselle & Sklar, LLP

(57) ABSTRACT

A method for tracking at least one medical marker is provided, wherein actual properties of the at least one marker are compared with nominal properties of the at least one marker. A basis for subsequent use of information obtained from the at least one marker is formed based on the comparison.

21 Claims, 3 Drawing Sheets

MEDICAL MARKER TRACKING WITH MARKER PROPERTY DETERMINATION

RELATED APPLICATION DATA

This application claims priority of U.S. Provisional Application No. 60/820,119 filed on Jul. 24, 2006, which is incorporated herein by reference in its entirety.

FIELD OF THE INVENTION

The invention relates to medical marker tracking wherein instrument or patient markers are detected by means of a medical marker tracking system.

BACKGROUND OF THE INVENTION

Marker tracking systems in general are used in medical technology to determine and track a position of treatment-assisting apparatus, instruments and/or parts of the patient's body. Using the positional data for the instruments, it is possible to perform medical navigation to assist physicians in treating the patient. This enables image-guided surgery to be implemented, in which physicians can see and check the position or their instruments relative to the position of treatment targets (e.g., parts of the patient's body) via a screen output, even if parts of the instruments are no longer visible. This also enables and/or greatly simplifies the planning of incisions. The data on the patient's anatomy can be obtained from previously or intra-operatively ascertained detections using imaging methods, e.g., computer tomography, nuclear spin tomography, x-ray imaging, etc., and via a registration procedure, can be incorporated into a coordinate system of an operating theater and/or the instrument tracking system. DE 196 39 651, for example, describes a surgical navigation system comprising marker tracking.

While using a tracking system, it often happens (particularly in orthopaedic operations) that the marker quality is impaired because the markers become partially or completely occluded, e.g., when soiled with water, blood or other incidental liquids or solids. When markers fail or their quality is impaired, this impairs the functionality or accuracy of marker tracking.

SUMMARY OF THE INVENTION

A medical marker tracking method is provided, wherein instrument or patient markers can be detected by means of a medical marker tracking system, and wherein actual properties of the markers are compared with nominal properties by means of a data processing unit. The result of the comparison forms the basis for subsequent use of the information on the detected markers.

In other words, marker quality may be checked during the tracking procedure. Using the information obtained from this check, it is possible to determine whether tracking can be performed to the required accuracy, such that if sufficient accuracy is no longer available, the conditions are in place to take appropriate measures. This is particularly advantageous because the treatment staff often do not notice marker quality impairments due to soiling (e.g., if the marker is only partially hidden or soiled only with a film of water). Accordingly, the method described herein can significantly improve the quality, safety and reliability of marker tracking systems.

The aforementioned "compared properties" can include the brightness, shape, size, visibility, degree of soiling and position (and/or position relative to a reference) of a marker and/or its image in the tracking system, or a combination of two or more of these properties. Other properties can include the brightness profile in the sensor data for the marker and the correlation of images of a marker from various viewing directions.

In stereoscopic systems, a property utilized for calculating the three-dimensional position is the so-called line-of-sight deviation or epipolar geometry, which ideally should be zero. If markers are soiled, the line-of-sight deviation is greater relative to ideal (e.g., well reflecting) markers. This follows from the fact that when markers are soiled, the focuses in the two two-dimensional camera images of a stereoscopic marker tracking system may be calculated at different positions. This can make it more difficult to triangulate to an exact point relative to data obtained from unsoiled markers. If, for example, a marker is only soiled in its left-hand region as viewed from the camera system, then the left-hand camera may calculate a two-dimensional center of area that is too far to the right. The right-hand camera will be less affected by this, because the soiling may not be visible from this camera. An attempt is then made by triangulation to spatially intersect the lines of sight belonging to each two-dimensional center of area. Essentially, this will only function (or only function well) when the focuses are precisely determined and the lines of sight intersect at exactly one point, namely the position of the marker. In reality, this is never exactly the case, but if the markers are good and the cameras are well calibrated, then very small, acceptable line-of-sight deviations are obtained. If the markers are poor (e.g., soiled, damaged, etc.), the line-of-sight deviations become greater. In other words, the line-of-sight deviation becomes a property of the markers condition, as line-of-sight deviation is dependent on marker properties. Even if the line-of-sight deviations of various markers in the tracking field relative to each other are considered, the line-of-sight deviation can be traced back to the quality of individual markers.

In order to track and check a specific marker over a period of time, it is advantageous to assign each marker a unique identifier in the tracking system. Further, the nominal properties of the markers can be stored in memory as base properties of markers, wherein base properties include properties of an unsoiled and/or new marker. The actual properties of the markers also can be periodically or continuously stored in such memory, wherein there exists the possibility of using previously stored actual properties as nominal properties. This enables sudden changes in the marker properties and/or marker quality to be detected.

If a comparison of shape is made, a typical brightness distribution of a marker over a pixel range of the marker image can be adduced for this purpose, and said marker image can be detected by a (video) image detection unit of the tracking system or a separate video detection unit that is assigned to the tracking system. The markers can be moved into the vicinity of an image detection unit of the tracking system in order to determine their properties, in order to make use of the greater scanning accuracy in this region.

The data processing unit and/or the memory assigned to the data processing unit can be provided as a separate unit or as part of the tracking system and/or as part of a medical navigation system assigned to the tracking system. There also exists the possibility, however, of partially processing the data on a number of these means.

A deviation in marker quality can be determined, for example, if the actual properties do not correspond to the nominal properties, in particular if the deviation is at or above a threshold value. The threshold value can be pre-defined or can be set by a user. Alternatively, the threshold value can be set, in particular automatically, for typical applications, after the data processing unit, for example, performs measuring procedures in the tracking system environment and/or a comparison of different markers is performed in the tracking system environment.

When a deviation in marker quality has been determined, different measures can be taken. These measures can include indicating the deviation in marker quality (e.g., visually on a screen, acoustically, etc.) or requesting the replacement of affected markers. It is also possible to (automatically) ensure that affected markers are no longer used by the tracking system, if this is feasible, e.g., if a corresponding redundancy is provided. Another option is to arithmetically correct the positional details defined by the markers, taking into account the quantitative deviations, in particular by recalculating the image center. In one case, for example, the image center can be re-ascertained by using the parts of the outer contour of the marker that are still available and match in the actual and nominal properties, in order to ascertain the image center, while parts of the contour that no longer match may be disregarded. Such a procedure can improve and/or restore the tracking accuracy, and can be inventively defined separately and independently of the method described above.

The tracking system can be a region sensor tracking system, in particular a CCD or CMOS sensor system, or a line scanning tracking system. Further, any type of medical tracking system may be utilized in conjunction with the method described herein. For example, it is possible to use optical tracking systems comprising passive reflecting markers or active emitting markers, magnetic tracking systems, ultrasound tracking systems, laser tracking systems or radar tracking systems, or combinations of two or more of these tracking systems.

Also provided herein is a program which, when it is running on a computer or is loaded onto a computer, causes the computer to perform a method such as described herein, and a computer program storage medium comprising such a program.

A medical marker tracking device comprises a medical marker tracking system that detects instrument or patient markers. The tracking device can further include a data processing unit comprising logic that compares actual properties of the markers with nominal properties and provides the result of the comparison as an output, for subsequent use of the information on the detected markers. All the features described herein and in the form of methods above can of course also be implemented in the form of devices.

BRIEF DESCRIPTION OF THE DRAWINGS

The forgoing and other features of the invention are hereinafter discussed with reference to the drawings.

DETAILED DESCRIPTION

Figure 1:
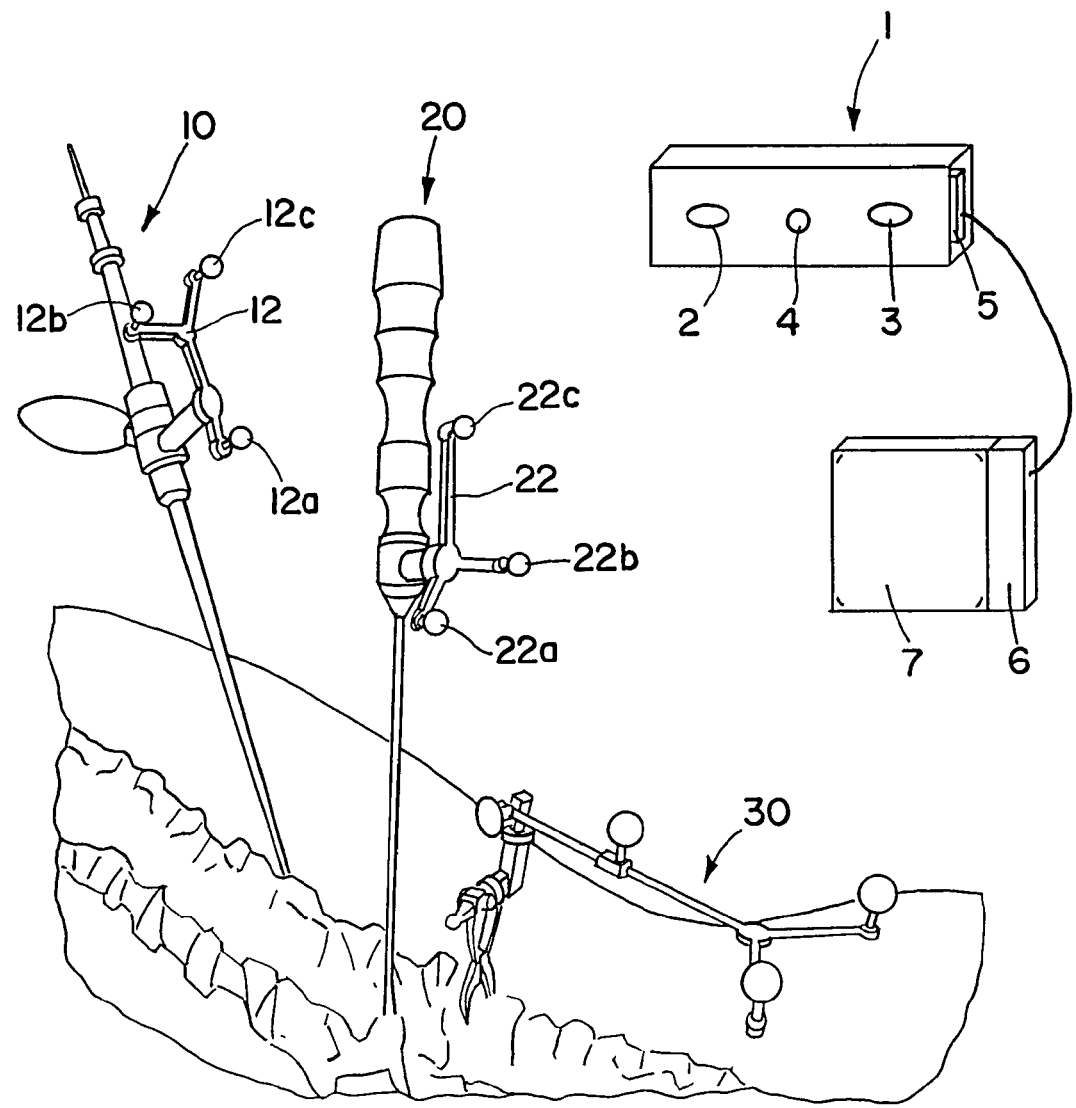
FIG. 1 is a schematic representation of an exemplary medical tracking system in accordance with the invention, comprising a connection to a medical navigation system.

FIG. 1 is an exemplary medical marker tracking environment, wherein instruments are shown that are used particularly in a navigated and image-assisted spinal treatment. Two instruments 10 and 20 include reference arrays 12 and 22, respectively, wherein the reference arrays 12 and 22 each have projecting arms bearing reflection marker spheres. Reference array 12 includes spheres 12a, 12b and 12c, while reference array 22 includes spheres 22a, 22b and 22c.

The markers on the reference arrays 12 and 22 are each provided in a characteristic arrangement that allows a specific instrument (in this case, the instrument 10 or 20) to be uniquely assigned to each of the arrangements.

A tracking system 1 and a navigation system 6 comprising a screen output 7 also are schematically shown in FIG. 1. The tracking system 1 includes a casing comprising two cameras 2 and 3 and an infrared light generator (e.g., a flash) 4. Infrared light flashes can be generated in very brief intervals by the infrared light generator 4 and then reflected by the reflecting markers on the reference arrays 12 and 22. These reflections may be detected by the stereoscopic cameras 2 and 3, and (after calibration) the tracking system 1 can calculate the spatial coordinates of the markers for the instruments 10 and 20. These calculated positional data can be relayed to the navigation system 6, which assigns the instruments 10 and 20 to the marker arrays 12 and 22 and reproduces their position in relation to the position of the patient's anatomy on the screen 7. The position of the patient's anatomy that is of interest (in this example, the spine) can be ascertained, for example, using a reference array 30.

A data processing unit 5, which is shown schematically, may be accommodated in the tracking system 1. The data processing unit 5 also can comprises a data memory, wherein data on the nominal properties of markers can be stored in the memory of the data processing unit 5. The data may pertain to how one or more of the markers 12a, 12b, and 12c, and/or 22a, 22b, and 22c should be imaged by the tracking system 1. The data, however, need not be stored in the tracking system 1 itself or in a data processing unit 5 assigned to the tracking system 1. Further, the data processing unit 5 may be provided separate from the tracking system 1, or it may be a data processing unit of the navigation system 6, for example.

The cameras 2 and 3 of the tracking system 1 both may ascertain positional data as point coordinates and perceive brightness values and shapes over certain pixel ranges. It is also possible to ascertain the brightness, size and visibility (e.g., visible or not visible), as well as degree of soiling from suitably combined information.

If these properties or a combination of these properties (actual properties) do not correspond to the given nominal properties, or the deviations exceed a threshold value, suitable measures can be taken. For example, the deviation or tracking error can be output on the screen 7 of the navigation system 6. Other options include requesting replacement of the marker in question or removing the marker from the calculation, if it is still possible to correctly navigate using the remaining markers.

Figure 2A:
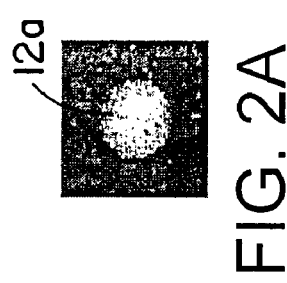
FIGS. 2A-2F illustrate different methods for ascertaining an image center (focus) for a marker image in accordance with the invention.
Figure 2B:
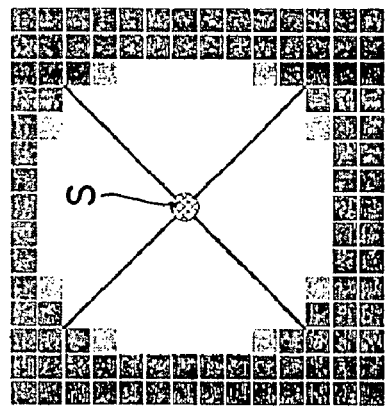

One option that lends itself when a deviation in marker quality has been determined is to recalculate the image center, which is also referred to below as the center of area or focus. The cameras 2 and 3 of the tracking system 1 can detect an image that extends over a number of pixels. In FIG. 2A, a marker 12a is shown as it would look in its base state, i.e., as a new or unsoiled marker. In the two enlarged representations of FIGS. 2B and 2C, it may be seen that when imaged, e.g., in the camera image, the marker 12a occupies a number of pixels at a certain brightness, and an upper region in the column designated as I shows how the focus (center of area) is conventionally determined. For this purpose, two straight lines that orthogonally intersect are introduced into the region of the bright pixels, and the position of the focus S and therefore the position of the image center is defined at the point of intersection. The corresponding positional coordinates of the marker 12a are then assigned to this point.

Figure 2C:
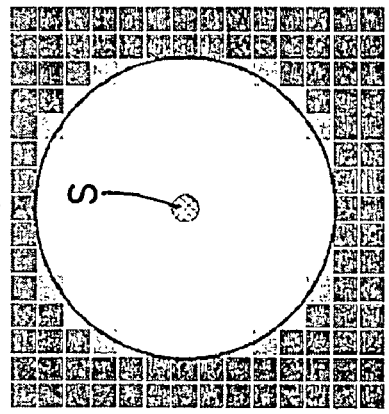
Figure 2D:
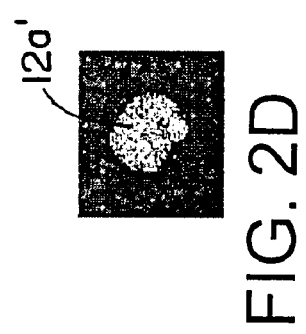
Figure 2E:
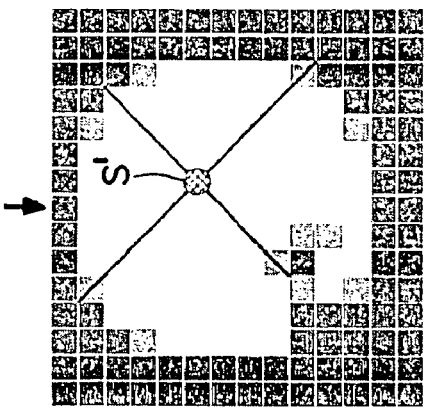

FIG. 2D shows a state that applies to a soiled marker. The lower left-hand end of the marker 12a' is soiled (for example by a bloodstain), reducing the brightness in this region. If the two intersecting straight lines are then inserted in the same way as above and form the point of intersection, this results in a center of area S' as shown in FIG. 2E, wherein the center is shifted out of the actual center of the marker 12a'. The resultant coordinates for the focus S' are erroneous and can lead to navigation and/or tracking defects.

Figure 2F:
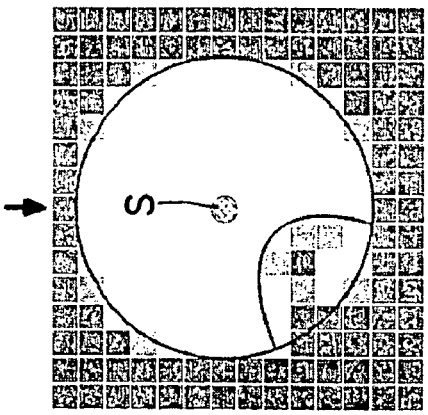

The column designated as II in FIGS. 2C and 2F then shows a solution, wherein the outer contour of the non-soiled marker 12a is ascertained, and in the present example the brightness distribution results in a circular contour. Given a contour defined in this way, which can be ascertained from the pixel brightness values with computer assistance, a unique center also can be ascertained, and in the present example, this center is the center point of the circle, which is in turn shown as the center of area S.

Although there are inconsistent and irregular brightness distributions in the lower left-hand region of the soiled marker 12a', the outer contour (i.e., the circular contour for the remaining region) can be accurately ascertained and/or assigned. This region, which enables a uniquely assignable contour to be ascertained, is then in turn used to determine the focus S. The remaining region can be excluded, wherein it is advantageous if expected marker image data (e.g., nominal properties) are stored in the tracking system 1, such that the remaining contour section used for determining the focus, with the assistance of this information, also can be ascertained. As can be seen in column II of FIG. 2F, such an arithmetic correction or determination places the focus back onto the correct point, and tracking and/or navigation can continue to be performed using correct positional data.

Accordingly, markers of a medical tracking system can be qualitatively classified based on various indicators ascertained, for example, from typical setups for tracking systems or from experiences with specific tracking systems. In other words, an expert system is provided that can take into account the following information and considerations.

1. The brightness of markers (e.g., reflection markers) should be within certain margins within the tracking volume of the tracking system. Since the spatial position of the markers can be ascertained by the tracking system, the expected brightness of a given marker can be compared with its actual brightness. The brightness of a marker depends on its shape (disc, sphere, cube, pyramid, . . . ), its size, and on the reflection properties and/or emission properties of its surface. In most applications, however, only one type of marker is used, or the types of marker are known from known or stored rigid body data sets for different instruments comprising different markers. An expert system can compare the expected brightness of a given marker at a given position in space with the actual brightness ascertained by the tracking system.

2. In addition, the system can use video images detected by the tracking system sensors to determine a typical brightness distribution of a marker over a set of pixels. If the marker is known to be round (sphere) or elliptical (disc marker) and the resolution of the sensor and/or sub-pixel algorithm performed on the sensor data allow unexpected shapes to be detected, this information can be used to define another quality criterion (property) of the marker.

3. Due to technical constraints, the resolution of older tracking systems may be low relative to newer systems, and edge detection or other shape recognition algorithms may not function particularly well, particularly when the markers are relatively far away from the sensors. In such cases, it is possible to determine the marker quality by moving the markers close to the camera of the tracking system. In this mode (close-up mode), the exact distances between the markers on their rigid body can be determined and any inaccuracies during the movement can be calculated. This provides a good indicator of whether potential problems with soiled markers may occur, even at a relatively low sensor resolution.

4. One typical problem in marker tracking is when a marker suddenly becomes soiled or wet during the treatment. Such sudden changes in the optical properties (brightness, color, shape) can be recognized by the tracking system as described herein. To this end, the tracking system can store the information collected from the marker, periodically or continuously over the period of use, and compare the newly detected properties in each case with previously detected data, wherein the tracking system can identify which marker of a data set corresponds to the marker in the other data set. Preferably, all of the markers are uniquely identified, wherein the system refers to the respective unique distances between markers on the reference array rigid bodies and has the option of maintaining a numbering of a marker during use, even if the instruments or the tracking system are moved.

The markers currently being used during navigation preferably are identified and their identification maintained, even if they are temporarily not visible. If, for example, the instrument is temporarily not visible due to an occlusion or because it is not currently being used, the identification of its markers (e.g., a numerical identifier) still remains valid when the instrument and/or markers re-enters the camera's field of view. Changes in the optical properties of the instrument markers can in turn be identified from one data set to the next, even over longer time intervals when the instrument has not been used for a particular time interval, e.g., when the instrument is being cleaned while the surgeon works with another instrument.

5. If high-resolution sensors are used and good sub-pixel image processing mechanisms are provided, the conventional focus ascertaining algorithms for estimating the position of the marker can be significantly improved. Combined with these new technologies from other technical fields, the detection of soiling on markers then can be further improved.

Based on the above considerations and technical embodiments, a full set of quality criteria can be defined for each marker, and the tracking system 1 can compare the criteria continuously and output warnings or other indications/information to the user as appropriate.

In summary, it may be said that problems with markers can be recognized that were not obvious with previous marker tracking systems. It becomes possible to detect sudden changes in the optical marker properties due to soiling of the markers, which applies to cases in which the markers are exposed to water (e.g., water droplets splashed on the surface of the marker) or other clear liquids/soils, which has otherwise not been easy for the users to recognize. It becomes possible to detect potential marker occlusions and to provide the user with quality information with regard to the tracking accuracy. This also increases the safety of the tracking and navigation systems, due to the increased accuracy and avoidance of incorrect position detection. It also improves the reliability of tracking and navigation systems, because information on the quality of the instrument tracking is provided.

Figure 3:
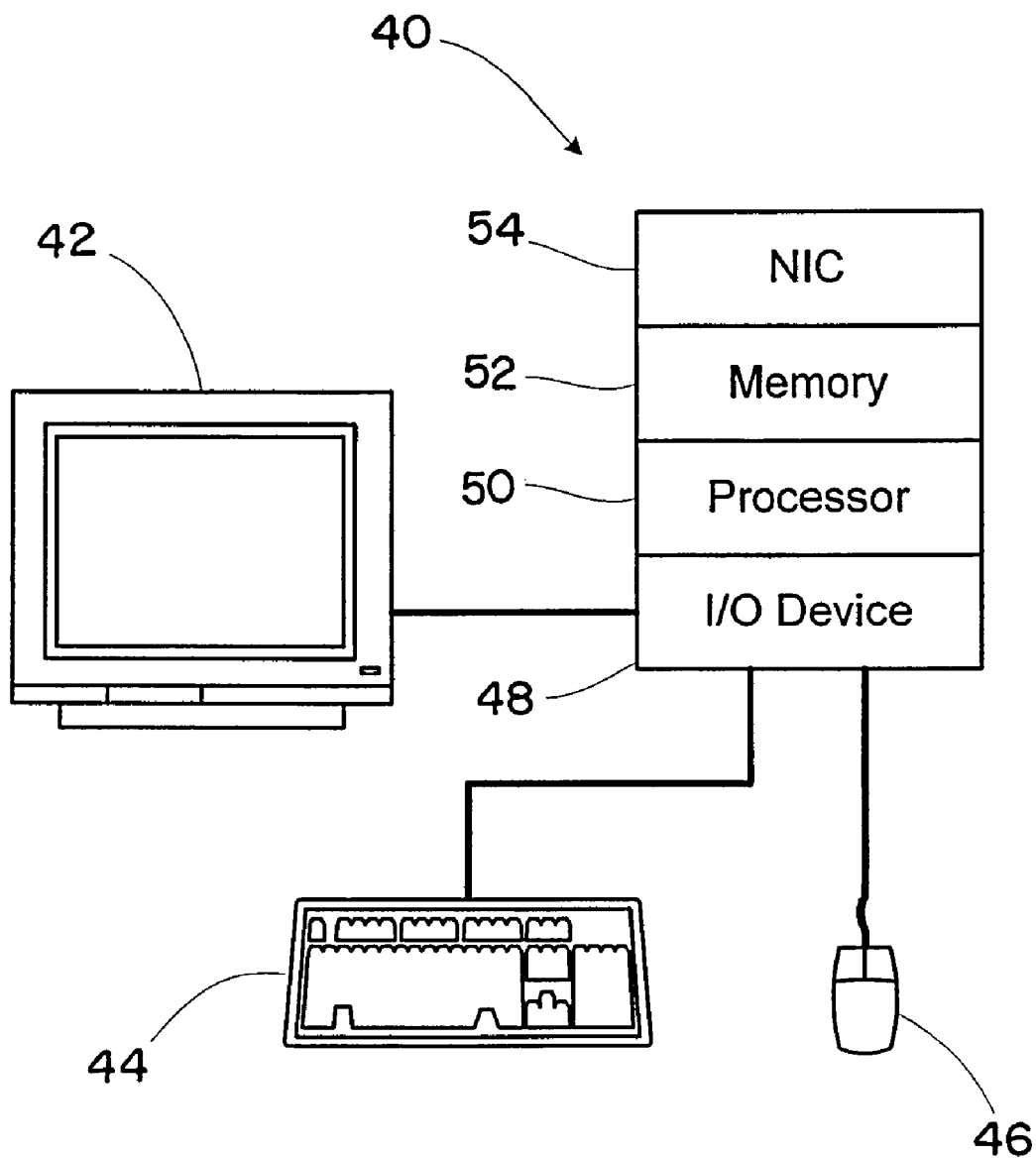
FIG. 3 is a block diagram of an exemplary computer system that can be used to carry out the method in accordance with invention.

FIG. 3 illustrates the exemplary computer system 40 that may be used to implement the method described herein (e.g., as a computer of the navigation system 6 and/or tracking system 1). The computer system 40 may include a display 42 for viewing system information (which may be in addition to the display 7, or may be the display 7), and a keyboard 44 and pointing device 46 for data entry, screen navigation, etc. A computer mouse or other device that points to or otherwise identifies a location, action, etc., e.g., by a point and click method or some other method, are examples of a pointing device 46. Alternatively, a touch screen (not shown) may be used in place of the keyboard 44 and pointing device 46. The display 42, keyboard 44 and mouse 46 communicate with a processor via an input/output device 48, such as a video card and/or serial port (e.g., a USB port or the like).

A processor 50, such as an AMD Athlon 64® processor or an Intel Pentium IV® processor, combined with a memory 52 execute programs to perform various functions, such as data entry, numerical calculations, screen display, system setup, etc. The memory 52 may comprise several devices, including volatile and non-volatile memory components. Accordingly, the memory 52 may include, for example, random access memory (RAM), read-only memory (ROM), hard disks, floppy disks, optical disks (e.g., CDs and DVDs), tapes, flash devices and/or other memory components, plus associated drives, players and/or readers for the memory devices. The processor 50 and the memory 52 are coupled together via a local interface (not shown). The local interface may be, for example, a data bus with accompanying control bus, a network, or other subsystem.

The memory may form part of a storage medium for storing information, such as application data, screen information, programs, etc., part of which may be in the form of a database. The storage medium may be a hard drive, for example, or any other storage means that can retain data, including other magnetic and/or optical storage devices. A network interface card (NIC) 54 allows the computer system 40 to communicate with other devices.

A person having ordinary skill in the art of computer programming and applications of programming for computer systems would be able in view of the description provided herein to program a computer system 40 to operate and to carry out the functions described herein. Accordingly, details as to the specific programming code have been omitted for the sake of brevity. Also, while software in the memory 52 or in some other memory of the computer and/or server may be used to allow the system to carry out the functions and features described herein in accordance with the preferred embodiment of the invention, such functions and features also could be carried out via dedicated hardware, firmware, software, or combinations thereof, without departing from the scope of the invention.

Computer program elements of the invention may be embodied in hardware and/or in software (including firmware, resident software, micro-code, etc.). The invention may take the form of a computer program product, which can be embodied by a computer-usable or computer-readable storage medium having computer-usable or computer-readable program instructions, "code" or a "computer program" embodied in the medium for use by or in connection with the instruction execution system. In the context of this document, a computer-usable or computer-readable medium may be any medium that can contain, store, communicate, propagate, or transport the program for use by or in connection with the instruction execution system, apparatus, or device. The computer-usable or computer-readable medium may be, for example but not limited to, an electronic, magnetic, optical, electromagnetic, infrared, or semiconductor system, apparatus, device, or propagation medium such as the Internet. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner. The computer program product and any software and hardware described herein form the various means for carrying out the functions of the invention in the example embodiments.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A method for tracking at least one medical marker, comprising:
    comparing, using a processor, actual properties of the at least one marker with nominal properties of the at least one marker; and
    forming a basis for subsequent use of information obtained from the at least one marker from the comparison,
    wherein comparing includes determining there is a deviation in quality of the at least one marker if the actual properties of the at least one marker do not correspond to the nominal properties of the at least one marker.

2. The method according to claim 1, further comprising assigning a unique identifier to the at least one marker.

3. The method according to claim 1, further comprising storing base properties of the at least one marker as nominal properties of the at least one marker.

4. The method according to claim 1, further comprising continuously or periodically storing actual properties of the at least one marker as nominal properties of the at least one marker.

5. The method according to claim 4, further comprising concluding properties of the at least one marker have changed when newly acquired actual properties of the at least one marker deviate from the nominal properties of the at least one marker.

6. The method according to claim 1, further comprising moving the at least one marker into a detection range of an image detection unit in order to determine properties of the at least one marker.

7. The method according to claim 1, wherein determining includes ascertaining there is a deviation in marker quality if the correspondence between the actual properties and the nominal properties deviates by a threshold value.

8. The method according to claim 7, wherein the threshold value is pre-defined or user settable.

9. The method according to claim 7, wherein the at least one marker is a plurality of markers, further comprising setting the threshold value based on a measuring procedure of the plurality of markers and/or a comparison of different markers of the plurality of markers.

10. The method according to claim 1, wherein the at least one marker is a plurality of markers, and once it is determined that a marker of the plurality of markers deviates in quality, then performing at least one of:
  indicating the deviation in marker quality;
  removing any marker that deviates in quality from tracking calculations;
  requesting replacement of the marker that deviates in quality; or
  arithmetically correcting positional details defined by the marker that deviates in quality.

11. The method according to claim 10, wherein arithmetically correcting includes recalculating the image center of the deviating marker.

12. The method according to claim 11, wherein recalculating the image center includes using a part of the deviating marker's outer contour that matches the actual and/or nominal properties of the deviating marker, and disregarding parts deviating marker's outer contour that do not match the actual and/or nominal properties.

13. A method for tracking at least one medical marker, comprising:
  comparing, using a processor, actual properties of the at least one marker with nominal properties of the at least one marker; and
  forming a basis for subsequent use of information obtained from the at least one marker from the comparison, wherein comparing includes comparing properties of at least one of
  a brightness or brightness profile in the at least one marker features,
  a shape of the at least one marker,
  a size of the at least one marker,
  a visibility of the at least one marker,
  a degree of soiling of the at least one marker,
  a correlation of images of the at least one marker from various viewing directions, the line-of-sight deviation or epipolar geometry, or
  a position or position relative to a reference of the at least one marker and/or an image of the at least one marker.

14. The method according to claim 13, wherein at least two properties are compared.

15. The method according to claim 13, wherein comparing properties based on shape includes adducing a typical brightness distribution of the at least one marker over a pixel range of the marker image.

16. A computer program embodied on a non-transitory computer readable storage medium for tracking at least one medical marker, comprising:
  code that compares actual properties of the at least one marker with nominal properties of the at least one marker; and
  code that forms a basis for subsequent use of information obtained from the at least one marker from the comparison,
  wherein the code that compares includes code that determines there is a deviation in quality of the at least one marker if the actual properties of the at least one marker do not correspond to the nominal properties of the at least one marker.

17. A medical marker tracking device, comprising:
  a medical marker tracking system operable to detect instrument or patient markers;
  a data processing unit and memory operatively coupled to said tracking system; and
  logic stored in memory and executable by said processor, said logic including
  logic that compares actual properties of the markers with nominal properties of the markers and provides the result of the comparison as an output for subsequent use of the information on the detected markers,
  wherein the logic that compares includes logic that determines there is a deviation in quality of the at least one marker if the actual properties of the at least one marker do not correspond to the nominal properties of the at least one marker.

18. The device of claim 17, wherein the data processing unit and/or the memory are separate from the medical marker tracking system.

19. The device according to claim 17, wherein the tracking system is a region sensor tracking system or a line scanning tracking system.

20. The device according to claim 19, wherein the region sensor tracking system is a CCD or CMOS sensor system.

21. The device according to claim 17, wherein the tracking system is at least one of an optical tracking system comprising passively reflecting markers, an optical tracking system comprising actively emitting markers, a magnetic tracking system, an ultrasound tracking system, a laser tracking system, or a radar tracking system.

* * * * *